United States Patent [19]

Ryan et al.

[11] Patent Number: 4,501,921

[45] Date of Patent: Feb. 26, 1985

[54] SYNTHESIS OF ALKYLIDENE INTERMEDIATES

[75] Inventors: Charles W. Ryan; Bruce A. Slomski, both of Indianapolis, Ind.

[73] Assignee: Eli Lilly and Company, Indianapolis, Ind.

[21] Appl. No.: 442,710

[22] Filed: Nov. 18, 1982

[51] Int. Cl.³ .................. C07C 143/75; C07C 143/86
[52] U.S. Cl. ...................................... 564/99; 544/159; 546/232; 548/542; 564/79; 564/97
[58] Field of Search ................ 544/159; 546/232; 548/542; 564/79, 97, 99

[56] References Cited

U.S. PATENT DOCUMENTS

| | | | |
|---|---|---|---|
| 3,840,527 | 10/1974 | Moore et al. | 564/97 X |
| 3,972,926 | 8/1976 | Moore et al. | 564/97 |
| 4,118,742 | 10/1978 | Paget et al. | 548/306 |

OTHER PUBLICATIONS

Morrison and Boyd, *Organic Chemistry*, 3rd Ed., pp. 512-513, (1973), Allyn and Bacon, Inc.
Wagner and Zook, *Synthetic Organic Chemistry*, p. 164, (1953), Wiley & Sons, Inc.
Suter et al., JACS 64, 2451 (1942).

*Primary Examiner*—Thomas A. Waltz
*Attorney, Agent, or Firm*—Joseph A. Jones; Arthur R. Whale

[57] ABSTRACT

A stereo-selective preparation of novel sulfonated o-phenylenediamines carrying a trans-α-alkylidenebenzyl group at the 5-position, which are intermediates in the synthesis of antiviral benzimidazoles.

16 Claims, No Drawings

SYNTHESIS OF ALKYLIDENE INTERMEDIATES

BACKGROUND OF THE INVENTION

1. Field of the Invention

This invention belongs to the fields of pharmaceutical and synthetic organic chemistry, and provides an improved process for preparing novel intermediates in the synthesis of anti-viral benzimidazoles. The intermediates are sulfonated o-phenylenediamines, and carry a trans-α-alkylidenebenzyl group at the 5-position.

2. State of the Art

The Benzimidazoles which are the ultimate products of the present process are taught by Paget, U.S. Pat. No. 4,118,742. The patent teaches a number of processes for the preparation of the benzimidazoles; its general process is to form the benzimidazole with the 1-position unsubstituted, and sulfonate as a final step.

The patent does not distinguish between the isomeric α-alkylidenebenzyl substituents of its compounds. See examples 72 and 74 of the patent, which do not discuss the isomeric form of the alkylidenyl substituents. It has since been discovered that the trans form of the alkylidenyl substituent is preferable, and the present process selectively forms the trans isomers. Neither does the patent suggest that the imidazole ring could as the final step, after the sulfonylamino and alkylidene groups had been selectively formed. U.S. Patent Application Ser. Nos. 373,944 and 373,945, of Ryan and Slomski, and of Dominianni, teach processes for preparing the starting compounds of the present process.

SUMMARY OF THE INENTION

The present process provides a compound of the formula

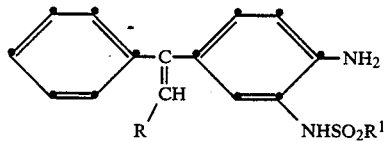

wherein R is methyl or ethyl;

$R^1$ is $C_3$-$C_5$ branched alkyl or $NR^2R^3$, wherein $R^2$ $R^3$ are independently $C_1$-$C_3$ alkyl, or combine with the nitrogen atom to which they are attached to form pyrrolidino, piperidiono or morpholino.

The invention also provides a process for preparing the above compounds, which process comprises reacting a benzoyl intermediate of the formula

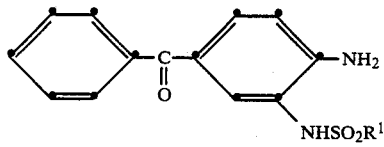

with a Grignard reagent of the formula

wherein X is bromo or chloro; in an oganic solvent suitable for Grignard reactions to form a hydroxy intermediate of the formula

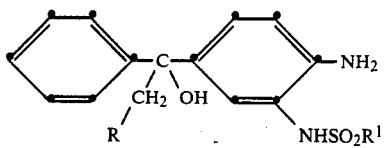

and dehydrating the hydroxy intermeidate with dilute acid.

DESCRIPTION OF THE PREFERRED EMBODIMENTS

All temperatures in this document are expressed in degrees Celsius.

The term $C_3$-$C_5$ branched alkyl and $C_1$-$C_3$ alkyl are used in their conventional meanings in organic chemistry, and include groups such as isopropyl, secondary butyl, tertiary butyl, isobutyl, neopentyl, 1-methylbutyl, 1-ethylpropyl and the like.

The following typical products of this invention are mentioned to assure that the reader fully understands the purpose of the invention.

trans-5-(α-ethylidenebenzyl)-$N^1$-isopropylsulfonyl-o-phenylenediamine trans-$N^1$-s-butylsulfonyl-5-(α-propylidenebenzyl)-o-phenylenediamine trans-$N^1$-t-butylsulfonyl-5-(α-ethylidenebenzyl)-o-phenylenediamine trans-5-(α-ethylidenebenzyl)-$N^1$-(2,2-dimethylpropylsulfonyl)-o-phenylenediamine trans-$N^1$-(2-methylbutylsulfonyl)-5-(α-propylidenebenzyl)-o-phenylenediamine trans-$N^1$-(1-ethylpropylsulfonyl)-5-(α-ethylidenebenzyl)-o-phenylaminediamine trans-5-(α-ethylidenebenzyl)-$N^1$-(1-methylbutylsulfonyl)-o-phenylenediamine trans-$N^1$-diethylaminosulfonyl-5-(α-propylidenebenzyl)-o-phenylenediamine trans-5-(α-ethylidenebenzyl)-$N^1$-methylpropylaminosulfonyl-o-phenylenediamine trans-5-(α-ethylidenebenzyl)-$N^1$-ethylpropylaminosulonyl-o-phenylenediamine trans-$N^1$-dipropylaminosulfonyl-5-(α-propylidenebenzyl)-o-phenylenediamine trans-5-(α-ethylidenebenzyl)-$N^1$-pyrroidinosulfonyl-o-phenylenediamine trans-$N^1$-piperidinosulfonyl-5-(α-propylidenebenzyl)-o-phenylenediamine trans $N^1$-morpholinosulfonyl-5-(α-propylidenebenzyl)-o-phenylenediamine.

The most preferred products are those wherein $R^1$ is isopropyl or $NR^2R^3$, especially wherein $R^2$ and $R^3$ are both methyl groups. The compounds wherein R is methyl are also preferred.

STARTING COMPOUNDS

The benzoyl starting compounds are preferably obtained by a process disclosed by Ryan and Slomski in U.S. Patent Application Ser. No. 373,944, which process is carried out by contacting the corresponding 4-benzoyl-o-phenylenediamine with the appropriate sulfonyl bromide or chloride, preferably the chloride, in any convenient solvent in the presence of at least about 1 mole of a pyridine base chosen from pyridine, the lutidines and the picolines, preferably pyridine.

The sulfonyl halides are readily obtained or prepared. The amount of the sulfonyl halide used in the reaction is of some importance. It has been observed that the use of a substantial excess of sulfonyl halide is likely to produce the undesired bissulfonyl compound, or the wrong mono-sulfonyl compound. Accordingly, only a modest excess of sulfonyl halide should be used, to assure that the phenylenediamine is fully consumed. It is preferred to use an amount of the sulfonyl halide from about 1 to about 1.2 mole per mole of the phenylenediamine, most preferably from about 1 to about 1.1 mole.

The type of organic solvent is not critical to the success of the process. The choice of solvent, of course, is intimately linked with the desired temperature of operation, and with the concentration at which the reaction is to be run. The best solvents for the process are the halogenated alkanes, such as chloroform dichloromethane, 1,2-dichloroethane and the like. Dichloromethane is a particularly preferred solvent. Other types of solvents, however, including aromatics, halogenated aromatics, esters, amides and nitriles may be used as is convenient. Aromatics, such as benzene, toluene and the xylenes, should be used only when the concentration of the reactants is to be low, because their solvency for the starting compound is not great. Esters such as ethyl acetate, ethyl formate, propyl acetate and the like are useful solvents, as are nitriles such as acetonitrile and propionitrile.

It is also entirely possible to use a sufficient amount of pyridine base to dissolve the reactants and operate without any other solvent. Such operation is not preferred, because of the difficulty of handling the basic wastes after the process is completed.

The process is run in the presence of at least about 1 mole of pyridine base per mole of phenylenediamine. It is preferred to use at least about 2 moles of the pyridine base, and still more preferred to use from about 4 to about 10 moles of the pyridine base per mole of phenylenediamine. Greater amounts of pyridine base may be used as desired. In general, it is found that the yield of the desired sulfonation product tends to increase slowyl with greater amounts of the pyridine base in the reaction mixture, and so the choice of the optimum amount of the pyridine base for a given process depends upon the relative costs of the pyridine base, compared to the other reactants, at the time and place in question.

The process is most preferably carried out at about the ambient temperature, which is considered to be from about 15° to about 35°. It may also be carried out effectively at temperatures in the preferred range from about 0° to about 50°, and temperature in a range from about 0° to about 100° may be used if desired in the circumstances. In general, it is observed that elevated temperatures tend to produce more of the undesired isomeric product, where the sulfonyl has added to the amino group para to the acyl group. However, operation even at elevated temperatures gives a substantial yield of the desired isomer.

The following preparation shows the synthesis of a preferred starting compound.

PREPARATION 1

5-benzoyl-$N^1$-isopropylsulfonyl-o-phenylenediamine

Twenty g. of 4-benzoyl-o-phenylenediamine was suspended in 150 ml. of dichloromethane and 30 ml. of pyridine, and 11 ml. of isopropylsulfonyl chloride was added dropwise while the temperature of the mixtures was held between 25° and 30°. the mixture was then stirred about 24 hours at 25°, and was washed with 150 ml. of 2N hydrochloric acid. The organic layer was then extracted with 190 ml. of 0.6N sodium hydroxide, and 100 ml. of isopropanol was added to the aqueous phase. The pH of the aqueous layer was adjusted to about 7.0 with concentrated hydrochloric acid, and the mixture was heated to reflux. The mixture was then stirred while it cooled overnight to 25°. It was then filtered and the solids were washed with 60 ml. of 33% aqueous isopropanol. The solids were dried in a vacuum oven at 50° for 8 hours to obtain 20.2 g. of the desired product, m.p. 150°–152° . High performance liquid chromatographic analysis indicated that the product was 98+% pure, showing a yield of 67.4% of the theoretical yield. The product was identified by its mass spectroscopic molecular ion, having a weight of 318, and by nuclear magnetic resonance (NMR) analysis on a 60-mHz instrument in CDCl$_3$ plus DMSOd$_6$, showing characteristic peaks at $\delta$1.3–1.4 (d, 6H, (CH$_3$)$_2$); 2.9–3.5 (m, 1H, CH), 5.5 (s, 2H, NH$_2$); 6.7–7.8 (m, 8H, aromatic).

PROCESS OF THE PRESENT INVENTION

The unique benefit of the present process is its ability to provide high yields of the desired trans isomer of its products. The process is carried out in two linked steps. In the first step, the benzoyl starting compound is alkylated with a Grignard reagent which provides the desired ethyl or propyl group, under conventional Grignard conditions. Grignard reagents wherein X is bromo are preferred. It is preferred to use a substantial excess of the Grignard reagent; about 4 to 6 moles of Grignard reagent is the preferred amount. At least about 4 moles of Grignard reagent should be used, and very large excess amounts do no harm.

The Grignard reaction is preferably carried out in diethyl ether, as is usually preferred for such reactions. Tetrahydrofuran is less highly preferred.

It will be noted from the following examples that co-solvents are advantageously used in the present process because of the low solubility of the products in the Grignard solvents. Such inert solvents as halogenated alkanes, such as dichloromethane, trichloroethane, chloroform and the like, halogenated aromatics such as chlorobenzene, the various chlorotoluenes and the like, and aromatic such as benezene, toluene, ethylbenzene and the like may be used.

The Grignard reaction is carried out at relatively low temperatures in the range from about −40° to about 50°, most preferably from about 0° to about 15°. Essentially complete reaction of the Grignard reagent is obtained in a few hours with moderate agitation.

It is important to maintain Grignard reactions in an anhydrous condition. Thus, equipment and solvent should be carefully dried before charging the equipment for the reaction, and the mixture should be protected during the reaction from moisture, as by maintaining an inert gas blanket in the equipment.

It is not necessary to isolate the hydroxy intermediate from the Grignard reaction. The reaction mixture may be added directly to dilute aqueous acid to obtain dehydration. The partial purification of the hydroxy intermediate before dehydration is entirely feasible if the operator desires it in the circumstances.

Example 14 below illustrates a procedure wherein the residual magnesium from the Grignard reagent is removed from the mixture with a chelating agent before dehydration. Such widely useful chelating agents as derivatives of ethylenediaminetetraacetic acid are appropriate when the procedure is used.

The dehydration step is preferably carried out with a strong acid such as hydrochloric acid or sulfuric acid. Organic acids such as acetic, formic, or propionic may also be used if convenient or economical, as can sulfonic acids such as methanesulfonic or toluenesulfonic acid. A sufficient amount of acid should be used to provide full contact of the organic reaction mixture with the acid phase, if aqueous acid is used, and the concentration of the acid should preferably be such as to provide an indicated pH in the range of 1. The dehydration is conveniently carried out at about ambient temperature; temperatures from about 0° to about 100° may be conveniently used as desired; high temperatures should be used when a relatively weak acid is used.

The product of the process of this invention is isolated easily by crystallization, preferably from toluene or isopropanol. It may easily be isolated as an alkali metal salt, such as a sodium, potassium or lithium salt, if desired. The examples below point out analytical methods which identify the desired isomeric form, and show that the desired isomer is obtained in excellent yield and purity according to the present invention.

Synthesis of the Benzimidazoles

Anti-viral benzimidazoles are prepared from the products of the present process by the usual synthetic methods, especially by reaction with cyanogen bromide to form the 2-aminobenzimidazoles, which are a particularly preferred class of the anti-viral compounds (see U.S. Pat. No. 4,118,742, column 8). It is particularly advantageous to form the benzimidazoles by forming the sodium or lithium salt of the product of this process, as by contact with concentrated aqueous sodium hydroxide, removing the water and adding cyanogen bromide, which forms the benzimidazole upon stirring at ambient temperature.

The following examples further illustrate the process of the present invention, providing the novel compounds of the invention.

EXAMPLE 1

Trans-5-(α-ethylidenebenzyl)-$N^1$-isopropylsulfonyl-o-phenylenediamine

A 2-liter 3-necked flask was equipped with a stirrer, thermometer, condenser with drying tube and dropping funnel. To the flask was added 500 ml. of 2-molar ethyl magnesium bromide in diethyl ether, and the contents were chilled to 0°. To the flask was then added 63.6 g. of 5-benzoyl-$N^1$-isopropylsulfonyl-o-phenylenediamine dissolved in 480 ml. of dichloromethane and 120 ml. of tetrahydrofuran; the solution was added dropwise, holding the temperature of the flask in the range 0° to 15°. After the addition was complete, the mixture was stirred at 0° to 5° for two hours. Then the reaction mixture was added dropwise with stirring to another similar flask charged with 670 ml. of water and 85 ml. of concentrated hydrochloric acid, while the temperature was held at from 0° to 15°. After the addition was complete, the pH of the acid mixture was adjusted to 1 by adding 13 ml. of additional concentrated hydrochloric acid. The mixture was then stirred at ambient temperature for 2.75 hours, and the organic layer was separated and washed twice with 250 ml. portions of water. The organic layer was then distilled at ambient pressure, and 450 ml. of condensate was removed and replaced with 450 ml. of toluene. The mixture was then allowed to stand at ambient temperature for about 16 hours, and was distilled again to a vapor temperature of 108°, liquid temperature 112°. Five hundred ml. condensate was removed. The liquid was then cooled slowly to ambient temperature with stirring, seeded with authentic product and chilled with stirring for 2-3 hours. It was then filtered, and the solids were washed with cold toluene and dried under vacuum at 40° to obtain 48.7 g. of the desired poduct, m.p. 130°-133°.

The product was analyzed by high performance liquid chromatography, using a Dupont Zorbax ODS column, and an ultraviolet detector at 268 nm. The eluting solvent was 65:35 methanol:water containing 1.4 g. of sodium acetate per liter. The analysis indicated that the product contained 95.7% of the desired trans isomer and 4.3% of the undesired isomer, indicating a corrected yield of 70.6% of the theoretical yield. Identity of the product was further confirmed by nuclear magnetic resonance analysis on a 60 mHz instrument in $CDCl_3$: $\delta$1.28 (d, 6H, $(CH_3)_2$); 1.69 (d, 3H, $CH_3$) 3.18 (m, 1H, CH) 4.30 (s, 2H, $NH_2$) 6.00 (q, 1H, CH); 6.5-7.33 (m, 8H, aromatic).

EXAMPLE 2

Trans-5-(α-ethylidenebenzyl)-$N^1$-isopropylsulfonyl-o-phenylenediamine

An apparatus similar to that of Example 1 was set up and charged with 228 ml. of 2.6-molar ethyl magnesium bromide in diethyl ether, and the solution was chilled to 0°. To it was added dropwise with stirring a solution of 38 g. of 5-benzoyl-$N^1$-isopropylsulfonyl-o-phenylenediamine in 285 ml. of dichloromethane and 76 ml. of tetrahydrofuran, while the temperature was held in the range of 0° to 10°. The complete mixture was then stirred for two hours at 0° to 5°. It was then added with stirring, over a period of 40 minutes, to 285 ml. of water and 46 ml. of glacial acetic acid at 0° to 15°, and the acid mixture was then stirred at ambient temperature for one hour and the organic layer was separated. To it was added 200 ml. of toluene, and the organic solution was distilled at ambient pressure until the liquid temperature reached 70°, at which time the vapor temperature was 58° and 400 ml. of condensate had been removed. The mixture was then stirred at 60° for one hour, and at ambient temperature for 16 hours. To it was added 200 ml. of water, and the pH was adjusted to 8.0-8.5 with ammonium hydroxide. Sodium chloride was added to assist in separation, and the organic layer was collected in a flask and was diluted with 200 ml. of toluene. The organic solution was then distilled at ambient pressure until the vapor temperature reached 102°, and the concentrated solution was then placed in an ice bath, seeded and stirred for four hours. The solids were filtered, washed with cold toluene and oven dried at 40° under vacuum to obtain 23.9 g. of the desired product, m.p. 132°-135°, substantially identical to the product of Example 1. Liquid chromatography showed that the product contained 96.2% of the desired isomer, a corrected yield of 58.3%.

EXAMPLE 3

Trans-5-(α-ethylidenebenzyl)-$N^1$-isopropylsulfonyl-o-phenylenediamine

A 500 ml. flask similar to that of Example 1 was charged with 90 ml. of 2.75-molar ethyl magnesium bromide in diethyl ether, and the solution was chilled to 0°. To it was then added a solution of 19 g. of 5-benzoyl-$N^1$-isopropylsulfonyl-o-phenylenediamine in 142 ml. of dichloromethane and 38 ml. of tetrahydrofuran, dropwise, holding the temperature at 0° to 15°, and the mixture was then stirred for two hours at 0° to 5°. The reaction mixture was then added dropwise to 300 ml. of water and 60 ml. of concentrated hydrochloric acid, with stirring, while the temperature was held at 0° to 15°, and the acid mixture was then stirred at ambient temperature for 2.5 hours. The organic layer was then separated and washed twice with 250 ml. portions of water, and was then distilled at ambient pressure until the liquid temperature reached 65° and the vapor temperature was 53°. To the residue was then added 200 ml. of isopropanol, and the distillation was continued until the remaining volume was about 100 ml. The residue was then allowed to cool to ambient temperature and was stirred for 16 hours and filtered. The solids were washed with isopropanol and dried under vacuum at 40° to obtain 11.3 g. of the desired product, m.p. 128°-131°, substantially identical to the product of Example 1. The product was found by liquid chromatography to contain 95.5% of the desired isomer; the corrected yield was 54.5% of the theoretical yield.

EXAMPLE 4

Trans-5-(α-ethylidenebenzyl)-$N^1$-isopropylsulfonyl-o-phenylenediamine

An apparatus like that of Example 3 was set up and charged with 120 ml. of 2.75-molar ethyl magnesium bromide in diethyl ether. The process was carried out according to the process of Example 3 above, to obtain 12.2 g. of the desired product, m.p. 130°-133°, containing 96.2% of the desired isomer by liquid chromatography. The corrected yield was 59.3% of the theoretical yield, and the product was substantially identical to the product of Example 1.

EXAMPLE 5

Trans-5-(α-ethylidenebenzyl)-$N^1$-isopropylsulfonyl-o-phenylenediamine

The process was carried out exactly according to Example 4, except that the amount of ethyl magnesium bromide solution was 180 ml. The dried product was 12.1 g. of the desired product, m.p. 132°-134°, containing 96.6% of the desired isomer, substantially identical to the product of Example 1. The corrected yield was 59.1% of the theoretical yield.

EXAMPLE 6

Trans-5-(α-ethylidenebenzyl)-$N^1$-isopropylsulfonyl-o-phenylenediamine

To 166 ml. of 3-molar ethyl magnesium bromide in diethyl ether at 0° was added a slurry of 31.8 g. of 5-benzoyl-$N^1$-isopropylsulfonyl-o-phenylenediamine in 240 ml. of dichloromethane, while the temperature was held at 0° to 15°. The mixture was then stirred for two hours at 0° to 10°. The reaction mixture was then added dropwise to 335 ml. of water and 42 ml. of concentrated hydrochloric acid, while the temperature of the mixture was held at 0° to 15°. The pH was then adjusted to 1.0 by adding 2.8 ml. of additional hydrochloric acid, and the acid mixture was stirred at ambient temperature for 3.5 hours. The organic layer was separated and washed with 250 ml. of water, and then with 250 ml. of saturated sodium bicarbonate solution. The washed organic solution was then distilled at ambient pressure until the pot temperature reached 58°. To it was then added 300 ml. of toluene, and it was distilled under vacuum to a total volume of about 150 ml. The end point temperature was 32° liquid, 28° vapor, at 45 mm. Crystallization began as soon as the vacuum was released, and the mixture was stirred at ambient temperature for 2.5 hours and filtered. The solids were washed with toluene and dried under vacuum at 40° to obtain 19.9 g. of the desired product, m.p. 131°-135°, substantially identical to the product of Example 1, containing 96.5% of the desired isomer by liquid chromatography. The corrected yield was 58.2% of the theoretical yield.

EXAMPLE 7

Trans-5-(α-ethylidenebenzyl)-$N^1$-isopropylsulfonyl-o-phenylenediamine

To 114 ml. of 2.6-molar ethyl magnesium bromide in diethyl ether at 0° was added dropwise a solution of 19 g. of 5-benzoyl-$N^1$-isopropylsulfonyl-o-phenylenediamine in 142 ml. of dichloromethane and 38 ml. of tetrahydrofuran, while the temperature was held at 0° to 15°. The mixture was then stirred for two hours at 0° to 5°, and to it was added dropwise with excellent cooling, a solution of 153 ml. of water and 20 ml. of concentrated hyrochloric acid. The temperature was held at 0° to 15° during the addition, which produced a very strong exotherm, especially at the beginning of the addition. After the addition the pH of the mixture was 1.0; after one-half hour of stirring it was necessary to add 14 ml. of additional hydrochloric acid to return the pH to 1.0. The mixture was then stirred at ambient temperature for one hour, and the organic layer was separated and washed with 250 ml. of water. The organic layer was then distilled at ambient pressure, collecting 150 ml. of condensate at a liquid temperature of 51° and vapor temperature of 44°. To the residue was added 150 ml. of toluene, and the distillation was continued until 160 ml. of additional condensate had been collected and the volume of the residue was about 100 ml. The liquid temperature was then 111° and the vapor temperature, 108°. The residue was then cooled with stirring and seeding, and was chilled in an ice bath and filtered. The solids were washed with cold toluene and dried at 40° under vacuum to obtain 10.1 g. of the desired product, m.p. 130°-133°, substantially identical to the product of Example 1. The yield was 51.0% of the theoretical yield.

EXAMPLE 8

Trans-5-(α-ethylidenebenzyl)-$N^1$-isopropylsulfonyl-o-phenylenediamine, sodium salt To 333 ml. of 3-molar ethyl magnesium bromide in diethyl ether at 0° was added 63.6 g. of 5-benzoyl-$N^1$-isopropylsulfonyl-o-phenylenediamine slurried in 480 ml. of dichloromethane, portionwise, keeping the temperature at 0° to 10°. The mixture was then stirred at 10° for two hours, and it was added dropwise to 370 ml. of water and 90 ml. of concentrated hydrochloric acid at 0° to 15°. The acid mixture was then stirred for 3.5 hours at ambient temperature, and the organic layer was separated and washed with 500 ml. of water, and then with 500 ml. of saturated sodium bicarbonate solution. One-half of the organic layer was added to a 1-liter flask, and was distilled at ambient pressure until the liquid temperature reached 60°. To it was then added 300 ml. of isopropanol, and the mixture was distilled down to 150 ml. volume. It was then cooled to 50°, and 5.4 ml. of 50% sodium hydroxide solution was added. The mixture was then cooled, seeded, and chilled for 2.5 hours with stirring. The solids were collected by filtration and washed with cold isopropanol, and dried under vacuum at 40° to obtain 29.4 g. of the desired product, substantially identical to the product of Example 1, containing 91.2% of the desired isomer in the form of the sodium salt, by liquid chromatography. The corrected yield was 65.1% of the theoretical yield.

EXAMPLE 9

Trans-5-(α-ethylidenebenzyl)-$N_1'$-isopropylsulfonyl-o-phenylenediamine, lithium salt The process of Example 8 was repeated, down to the point where the mixture was distilled down to 150 ml. volume. The resulting residue was diluted by the addition of 180 ml. of isopropanol, and 21.8 ml. of 4.6N aqueous lithium hydroxide was added at 50° and stirred vigorously at constant temperature until solution was obtained. It was then stirred slowly and allowed to cool to ambient temperature, and then seeded with authentic product and chilled in an ice bath for five hours. The precipitate was collected and washed with cold 90% aqueous isopropanol. The washed filter cake was oven dried overnight under vacuum at 40° to obtain 20 g. of the desired product, which was found by high performance liquid chromatography to be 95% pure and to contain only 3.1% of the cis isomer.

EXAMPLE 10

Trans-N'-dimethylaminosulfonyl-5-(α-ethylidenebenzyl)-o-phenylenediamine

Ninety ml. of 2.5-molar ethyl magnesium bromide in diethyl ether was cooled to 0°, and to it was added 9.6 g. of 5-benzoyl-$N^1$-dimethylaminosulfonyl-o-phenylenediamine dissolved in 50 ml. of tetrahydrofuran and 50 ml. of dichloromethane. The temperature was held at 0° to 5° during the addition, and the mixture was then stirred at ambient temperature for two hours. It was added to 125 ml. of cold 2N hydrochloric acid, holding the temperature at 25° maximum during the addition. The acid mixture was then stirred one hour at 25°, and the layers were separated. The organic layer was then washed with saturated aqueous sodium bicarbonate solution, and then with saturated aqueous sodium chloride solution and dried over magnesium sulfate. The organic solution was then concentrated under vacuum, and 55 ml. of toluene was added to the residue and stirred at ambient temperature overnight. The mixture was then filtered, and the solids were washed with cold toluene and dried under vacuum to obtain 6.0 g. of the desired product, m.p. 130°–133°. The yield was 60.4% of the theoretical yield, and nuclear magnetic resonance analysis of the product on a 60 mHz instrument in $CDCl_3 + DMSOd_6$ shows only the desired trans isomer: δ1.67 (d, 3H, $CH_3$); 2.63 (s, 6H, $(CH_3)_2$); 4.27 (s, 2H, $NH_2$) 6.02 (q, 1H, CH) 6.33–7.67 (m, 8H, aromatic).

EXAMPLE 11

Trans-$N^1$-isopropylsulfonyl-5-(α-propylidenebenzyl)-o-phenylenediamine

To 227 ml. of 2.2-molar propyl magnesium bromide in diethyl ether at 0° was added a slurry of 31.8 g. of 5-benzoyl-$N^1$-isopropylsulfonyl-o-phenylenediamine in 240 ml. of dichloromethane, holding the temperature at 0° to 10°. The addition was in a period of 30 minutes. The mixture was then stirred at 5° for two hours, and was added dropwise to a solution of 335 ml. of deionized water and 42.5 ml. of concentrated hydrochloric acid at 0°. The addition time was 45 minutes. The pH of the mixture was then adjusted to 1.0 by the addition of additional hydrochloric acid, and the mixture was warmed to ambient temperature with stirring for 2.5 hours. The organic layer was then separated and washed with 250 ml. of water and then with 250 ml. of sodium bicarbonate solution. The mixture was then distilled at ambient pressure until the liquid temperature reached 50°. Three hundred ml. of toluene was then added, and the solvent was removed under vacuum to obtain 34.9 g. of residue, which was dissolved in hot isopropanol, and the solution was divided into two equal parts of 120 ml. each. One section was seeded with authentic product and chilled for three days, and filtered to obtain a solid. The product was washed with ice cold isopropanol and dried overnight at 40° under vacuum to obtain 6.5 g. of the desired product, m.p. 104°–106°. High performance liquid chromatography indicated that the product was 97.0% pure, containing only 1.9% of the cis isomer.

EXAMPLE 12

Trans-$N^1$-isopropylsulfonyl-5-(α-propylidenebenzyl)-o-phenylenediamine

To 150 ml. of 2.2-molar propyl magnesium bromide solution in diethyl ether at 0° was added 20 g. of 5-benzoyl-$N^1$-isopropylsulfonyl-o-phenylenediamine in 170 ml. of tetrahydrofuran, while the temperature was held at 0° to 5°. The mixture was allowed to warm to ambient temperature with stirring overnight. The mixture was then poured into one liter of saturated ammonium chloride solution at 22°–25°, and the pH was then adjusted to 7.2. The organic layer was then separated, and the aqueous layer was extracted twice with 300–350 ml. portions of chloroform. The organic layers were combined, dried over magnesium sulfate and evaporated under vacuum to an oil, which was added to 250 ml. of chloroform and 13.2 g. of p-toluenesulfonic acid. The mixture was stirred under reflux for 3.5 hours and cooled to ambient temperature. It was then washed with two 300 ml. portions of water, with 300 ml. of saturated sodium bicarbonate solution, and again with water. The organic layer was then dried over magnesium sulfate and evaporated under vacuum to a brown oil, which was identified by converting it to the corresponding anti-viral benzimidazole in the following preparation.

PREPARATION 2

Trans-2-amino-1-isopropylsulfonyl-6-(α-propylidenebenzyl)benzimidazole

To the oil obtained in Example 12 were added 600 ml. of water and 58 ml. of 1N sodium hydroxide. The solution obtained was filtered, and the filtrate was stirred while 6.2 g. of cyanogen bromide was added. The mixture was stirred overnight, and the aqueous solution was poured off. The organic material adherent to the stirrer was dissolved in methanol, and the methanol was removed under vacuum, leaving a solid residue which was dissolved in a small amount of hot methanol. Crystalline product formed spontaneously, and part of the methanol was removed under vacuum to obtain 5.9 g. of crystalline product, which was recrystallized from isopropanol.

An additional 2.2 g. of crystalline product was obtained as another crop from the methanol solution. Analysis of the product by nuclear magnetic resonance on a 270 mHz instrument indicated that the desired product was obtained: $\delta 1.00$ (t,3H,CH$_3$); 1.25 (d),6H,(CH$_3$)$_2$); 2.05 (q,2H,CH$_2$); 3.8 (m,H,CH); 6.0 (t,H,CH); 6.8–8 (m, aromatic).

EXAMPLE 13

Trans-N$^1$-isopropylsulfonyl-5-($\alpha$-propylidenebenzyl)-o-phenylenediamine

A 9.54 g. portion of 5-benzoyl-N$^1$-isopropylsulfonyl-o-phenylenediamine in 150 ml. of tetrahydrofuran was held at 45° under nitrogen, and to it was added 70 ml. of 2.2-molar propyl magnesium chloride in diethyl ether. A strong exotherm occurred, and an ice bath was needed to control the temperature at 45°. The mixture was then stirred for 3.5 hours at 30°–40°, and was then poured into one liter of pH 4 buffer. The mixture was then adjusted to pH 4.5 with 1N hydrochloric acid, and the organic layer was separated. Sodium chloride was used to assist the separation. The aqueous layer was extracted with ethyl acetate, and the organic layer was combined with the first organic layer, dried over magnesium sulfate and reduced to a foam under vacuum. The foam was treated with chloroform, and the remaining precipitate was filtered off. The solution was combined with 5.7 g. of p-toluene-sulfonic acid, and stirred overnight under reflux. The mixture was then cooled, washed three times with water, dried over magnesium sulfate and reduced to a residue under vacuum. The product was identified in Preparation 3 by conversion to the corresponding benzimidazole.

Preparation 3

Trans-2-amino-1-isopropylsulfonyl-6-($\alpha$-propylidenebenzyl)benzimidazole

The residue obtained above was dissolved in 100 ml. of 1,2-dichloroethane, and 2.5 g. of 50% sodium hydroxide solution was added. The mixture was stirred under reflux and the water was removed with a Dean Stark trap. The mixture was then cooled to ambient temperature, and 3.2 g. of cyanogen bromide was added and the mixture was stirred overnight. Then it was heated and the dichloroethane was distilled off, and replaced with methanol. The solution was then concentrated to a residue, and the residue was dissolved in toluene and heated under reflux. The toluene was then removed to obtain an oil, which was dissolved in dichloromethane and dried onto 45 g. of silica gel. The silica gel was loaded onto a 75×5 cm. column, and eluted with dichloromethane. The fractions containing the product were combined, and the solvent was evaporated to obtain an oil, which was dissolved in methanol. A solid formed, and was collected and found by high performance liquid chromatography to be a 1:1 mixture of the desired trans isomer and the cis isomer. Evaporation of the methanol filtrate produced additional solid which was also a mixture of the isomers.

EXAMPLE 14

Trans-5-($\alpha$-ethylidenebenzyl)-N$^1$-isopropylsulfonyl-o-phenylen ediamine

To 250 ml. of 0.5-molar ethyl magnesium chloride in tetrahydrofuran at 0° was added a slurry of 31.8 g. of 5-benzoyl-N$^1$-isopropylsulfonyl-o-phenylenediamine in 250 ml. of dichloromethane, holding the temperature at 10° to 20° during the addition. The mixture was stirred for 2 hours at 10° to 15°, and was added dropwise to a solution of 350 ml. of water, 180 ml. of 50% sodium hydroxide and 264 g. of ethylenedinitrilliotetraacetic acid at 5° to 15°. The pH was then adjusted to 8.5 by the addition of acetic acid, and the organic layer was separated and washed with 500 ml. of saturated sodium bicarbonate solution. The organic layer was then evaporated under vacuum to obtain 37 g. of a sticky residue, which was dissolved in 200 ml. of dichloromethane with stirring. Two hundred ml. of water was added, and the pH of the mixture was adjusted to 0.5 with concentrated hydrochloric acid. The mixture was then stirred for 5.5 hours at ambient temperature, and the organic layer was separated and washed with 250 ml. of water and then with 250 ml. of saturated sodium bicarbonate solution. The organic layer was then distilled at ambient pressure until the liquid temperature reached 60°, and then 300 ml. of toluene was added. The mixture was then distilled under partial vacuum down to 125 ml. volume, and was then stirred overnight at ambient temperature and then for two hours in an ice bath to obtain a solid product, which was collected and washed with cold toluene. After oven drying under vacuum at 40°, the product was found to amount to 7.9 g., m.p. 130°–133°. Analysis by high performance liquid chromatography indicated that the product contained 98.0% of the desired isomer.

We claim:

1. A process for preparing a compound of the formula

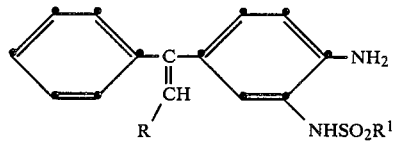

wherein R is methyl or ethyl;

R$^1$ is C$_3$–C$_5$ branched alkyl or NR$^2$R$^3$, wherein R$^2$ and R$^3$ are independently C$_1$–C$_3$ alkyl, or combine with the nitrogen atom to which they are attached to form pyrrolidino, piperidino or morpholino;

which process comprises reacting a benzoyl intermediate of the formula

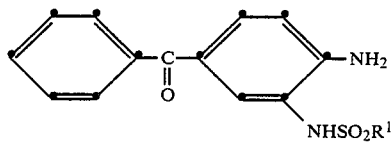

with a Grignard reagent of the formula
RCH$_2$MgX wherein X is bromo or chloro;

in an organic solvent suitable for Grignard reactions to form a hydroxy intermediate of the formula

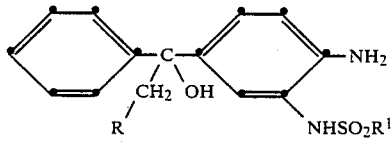

and dehydrating the hydroxy intermediate with dilute acid.

2. A process of claim 1 for preparing a compound wherein $R^1$ is isopropyl or $NR^2R^3$.

3. A process of claim 1 for preparing a compound wherein R is methyl.

4. A process of claim 2 for preparing a compound wherein R is methyl.

5. A process of claim 1 wherein at least about 4 moles of the Grignard reagent is used per mole of the benzoyl intermediate.

6. A process of claim 5 wherein the Grignard reagent is a compound wherein X is bromo.

7. A process of claim 6 wherein from about 4 to about 6 moles of the Grignard reagent is used per mole of the benzoyl intermediate.

8. A process of claim 5 wherein the reaction with the Grignard reagent is at from about −40° to about 50°.

9. A process of claim 7 wherein the reaction with the Grignard reagent is at from about −40° to about 50°.

10. A process of claim 5 wherein the reaction with the Grignard reagent is at from about 0° to about 15°.

11. A process of claim 9 wherein the reaction with the Grignard reagent is at from about 0° to about 15°.

12. A process of claim 5 wherein the dehydration is accomplished with aqueous acid.

13. A process of claim 11 wherein the dehydration is accomplished with aqueous acid.

14. A process of claim 6 wherein the reaction with the Grignard reagent is at from about 0° to about 15°.

15. A process of claim 13 for preparing a compound wherein R is methyl.

16. A process of claim 15 for preparing the compound wherein $R^1$ is isopropyl.

* * * * *